United States Patent [19]

Barford et al.

[11] Patent Number: 4,835,148

[45] Date of Patent: May 30, 1989

[54] SHAMPOO COMPOSITIONS COMPRISING WATER-INSOLUBLE PARTICULATE ANTI-INFLAMMATORY AGENTS

[75] Inventors: Brian D. Barford, West Chester; Andrew W. Fulmer, Loveland; Gary L. Manring, Oxford, all of Ohio

[73] Assignee: The Procter & Gamble Co., Cincinnati, Ohio

[21] Appl. No.: 833,638

[22] Filed: Feb. 24, 1986

[51] Int. Cl.$^4$ ............................................. A61K 31/56
[52] U.S. Cl. .................................... 514/179; 514/881
[58] Field of Search ........................................ 514/179

[56] References Cited

U.S. PATENT DOCUMENTS

| | | | |
|---|---|---|---|
| 3,238,102 | 3/1966 | Tanaka et al. | 514/179 |
| 3,527,864 | 9/1970 | McMillan et al. | 424/177 |
| 3,839,566 | 10/1974 | McMillan et al. | 424/243 |
| 3,881,000 | 4/1975 | Friedmann et al. | 424/209 |
| 4,450,151 | 4/1984 | Shinozawa | 424/46 |
| 4,552,872 | 11/1985 | Cooper et al. | 514/175 |
| 4,557,934 | 12/1985 | Cooper | 424/128 |

OTHER PUBLICATIONS

Handbook of Nonprescription Drugs, 5th Ed., (1977), pp. 328–330, 338 and 339.
"Adsorption of Polymer JR on Keratinous Surfaces—Part II", E. D. Goddard, Ph.D., et al., J. Soc. Cosmet. Chem., 26, pp. 539–550, (Nov. 1975).

*Primary Examiner*—Douglas W. Robinson
*Assistant Examiner*—Joseph A. Lipovsky
*Attorney, Agent, or Firm*—Douglas C. Mohl; Steven J. Goldstein; Leonard Williamson

[57] ABSTRACT

The present invention relates to shampoo compositions comprising at least about 0.1% of a water insoluble anti-inflammatory agent, from about 5% to about 40% of a synthetic surfactant and water.

9 Claims, No Drawings

SHAMPOO COMPOSITIONS COMPRISING WATER-INSOLUBLE PARTICULATE ANTI-INFLAMMATORY AGENTS

TECHNICAL FIELD

The present invention relates to shampoo compositions, lotions as well as concentrates and creams, comprising an effective amount of a particulate, water-insoluble anti-inflammatory agent.

BACKGROUND OF THE INVENTION

The present invention relates to improved treatment of dandruff, itch or other skin disorders involving excessive or abnormal shedding of dead epidermal cells from the scalp. Dandruff is a condition involving an increased rate of shedding of scales from the scalp wherein the scales are shed in large clumps. The scales appear dry and white or grey and are usually seen in small round patches on the crown of the head. In some cases the patches may cover the entire scalp. Itching is an occasional complaint; however, the primary concern is the unsightly appearance of the scales. In seborrheic dermatitis, there is a greater increase in the shedding of skin than with dandruff. This condition is marked by inflammation and increased itching. In psoriasis, there is chronic inflammation characterized by well-defined pink or red lesions covered with silvery scales.

It is known in treatment of the above disorders that increased cleaning and/or topical application of certain agents reduces scaling and inflammation.

Anti-inflammatory agents have long been used for the treatment of various skin and scalp disorders such as psoriasis, seborrhea, dermatitis, dandruff, and the like. However, these compounds have generally been available in non-rinse vehicles which contain oils or emulsions which would give the hair a soiled appearance.

Adrenal corticosteroids, and the synthetic analogues thereof, are some of the most useful pharmaceutical actives known in the art. These compounds have the capacity to prevent the development of, or suppress existing, localized heat, redness, tenderness and swelling which characterizes any inflammation of skin or mucous membrane. The utility of these compounds is shown in a clinical setting by the fact that cortiocosteroids inhibit this inflammatory response whether the inciting cause or agent is radiant, mechanical, chemical, infectious or immunological. Since the first recognition of the potent anti-inflammatory properties of these compounds in 1949, their therapeutic uses have increased dramatically. The unique biochemical, pharmacologic and physiologic properties of cortiocosteroids make them extremely useful in the topical treatment of inflammatory conditions. Several patent references disclose representative compositions.

U.S. Pat. No. 4,343,798, Fawzi, issued Aug. 10, 1982, describes topical antimicrobial/anti-inflammatory compositions containing $C_5$–$C_{12}$ fatty acids in combination with cortiocosteroids.

U.S. Pat. No. 3,934,013, Poulsen, issued Jan. 20, 1976, describes topical pharmaceutical compositions containing at least two cortiocosteroids, propylene glycol, a fatty alcohol and water. The patentee describes the "fatty alcohol ingredient" as any fatty alcohol having from 16-24 carbon atoms and, preferably, as a saturated, monohydric primary alcohol such as cetyl alcohol, or stearyl alcohol.

U.S. Pat. No. 4,289,764, Yarrow, et al, issued Sept. 15, 1981, describes topical pharmaceutical compositions with increased shelf stability. These compositions comprise a steroid, 15–50% by weight propylene glycol and are buffered to a pH of 2.7–3.3. The specification describes the desirability of thickening the propylene glycol (due to its low viscosity) with a compound selected from long-chain paraffins, fatty alcohols, and waxes, including cetyl stearyl alcohol, white soft paraffin and liquid paraffin.

U.S. Pat. No. 4,070,462, Ecker, issued Feb. 24, 1978, discloses a topical vehicle which includes (i) 5–15% 1,2-propanediol, 2,3-butanediol or 2-methyl-2,4, propanediol; (ii) 1–3% propylene glycol monostearate; and (iii) petrolatums and waxes to 100%.

The compositions described in these references are all left on the skin. They therefore do not suggest the advantages and the problems associated with a rinse-off product, such as a shampoo.

U.S. Pat. No. 3,881,000, Friedmann et al, discloses bis(phosphoylated)anthralin compounds for use in the treatment of psoriasis. Anti-inflammatories such as cortisone, hydrocortisone, hydrocortisone acetate, and prednisolone are disclosed as auxiliary agents in lotions, ointments, and shampoos of the invention.

While a shampoo composition is disclosed in Friedmann, there is no suggestion that only water-insoluble, particulate anti-inflammatory would provide deposition in effective therapeutic amounts. It is desirable therefore to provide shampoo such as lotions containing particulate anti-inflammatories.

Lotion shampoos, both antidandruff as well as non-dandruff types, are disclosed in the art. U.S. Pat. No. 3,917,817, Vanlerberghe et al., issued Nov. 5, 1975, discloses a shampoo composition containing a piperazine based cationic polymer, 10% sodium alkyl sulfate, 4% lauryl monoethanolamide and 3% glycol distearate. U.S. Pat. No. 4,013,787, Vanlerberghe et al., issued Mar. 22, 1977, discloses a similar composition. Japanese Application, with Open for Public Inspection No. 60810, May 19, 1977 (Lion Fat & Oil), discloses shampoos containing 5% to 50% of an anionic surfactant, 1% to 10% of a fatty acid diethanol amide, 0.1% to 10% of an insoluble fine powder, and 1% to 10% of an ethyleneglycol ester. U.S. Pat. No. 4,470,982, Winkler, issued Sept. 11, 1984, discloses lotion antidandruff shampoos containing ethyleneglycol esters and an antidandruff agent.

While these references, all of which are incorporated herein by reference, disclose compositions which contain components similar to those present in the compositions of the present invention, they do not suggest the advantages found by the present inventor for the compositions disclosed herein.

It is an object of the present invention to provide shampoo compositions which provide deposition of an effective amount of a water-insoluble particulate anti-inflammatory agent.

It is a further object of the present invention to provide a consumer acceptable suspension system capable of suspending an effective amount of the anti-inflammatory in a lotion shampoo.

It is a further object of the present invention to provide shampoo compositions containing safe and effective amounts of a water-insoluble, particulate anti-inflammatory and a second anti-dandruff agent.

These and other objects will become more apparent from the detailed description below.

SUMMARY OF THE INVENTION

The present invention relates to shampoo compositions comprising at least about 0.1% of a water-insoluble particulate anti-inflammatory agent, from about 5% to about 40% of a synthetic surfactant, and water.

DETAILED DESCRIPTION OF THE INVENTION

The compositions of the invention are shampoo compositions which are applied to wetted, lathered hair, worked through, and then rinsed off after a period of time.

ESSENTIAL INGREDIENTS

Water-Insoluble Particulate Anti-inflammatory

The compositions of the invention comprise at least about 0.1% of a water-insoluble particulate anti-inflammatory agent. Preferably the amount is from about 0.1% to about 5%, more preferably from about 0.2% to about 2%.

Any type of known anti-inflammatory agent may be useful in compositions of the present invention so long as they may be formed into a water-insoluble particulate compound. It is critical for the present invention that the anti-inflammatory agent be an insoluble particulate. Soluble analogues are not as effective in the present compositions. The term water-insoluble when used herein means that 90% or more of the material will remain insoluble in an aqueous system at 25° C., preferably 95% or more when used in compositions of the invention.

Without wishing to be bound by theory, it is believed that the effectiveness of the insoluble particulates is due to the increased deposition on the scalp. Anti-inflammatory agents in insoluble particulate form come out of suspension when diluted by application to wetted hair, and deposit on the hair and scalp. When the composition is rinsed from the hair, many particles of the agent remain on the hair and scalp to provide an effective amount for treatment. A soluble anti-inflammatory agent, for the most part, rinses away when the composition is rinsed from the hair, providing only an ineffective amount remaining on the scalp. Compositions of the invention can provide up to ten times the deposition of soluble analagous, anti-inflammatory agents.

A preferred category of anti-inflammatory agents are the adrenal corticosteroids. Most preferred is hydrocortisone acetate, a known anti-inflammatory agent which exists and is commercially available in insoluble particulate form.

Surfactant

An essential component of the present compositions is a surfactant. The surfactant, which may be selected from any of a wide variety of synthetic anionic, amphoteric, zwitterionic and nonionic surfactants, is present at a level of from about 5% to about 40%, from about 15% to about 25% for lotion shampoos.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sacrosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

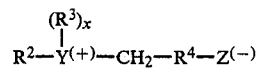

$$R^2-Y^{(+)}-CH_2-R^4-Z^{(-)}$$
with $(R^3)_x$ on $Y$ wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, lauryl bis-(2-hydroxypropyl)alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl)sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxy-ethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:

dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:

octadecyl methyl sulfoxide, 2-ketotridecyl methyl sulfoxide, 3,6,9,-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in McCutcheon's, Detergents and Emulsifiers, 1983 Annual, published by Allured Publishing Corporation, which is incorporated herein by reference.

The above-mentioned surfactants can be used alone or in combination in the shampoo compositions of the present invention. The anionic surfactants, particularly the alkyl sulfates, the ethoxylated alkyl sulfates and mixtures thereof are preferred for use herein as well as the amido betaines.

Water

Water is the remaining essential ingredient of the present compositions. The compositions of the invention contain from about 50% to about 95% water, preferably from about 60% to about 75%.

OPTIONAL COMPONENTS

Anti-dandruff Agents

In one preferred embodiment, additional anti-dandruff agents are also elements of the shampoo compositions herein. Included among such agents are coal tar, sulfur, selenium sulfide, salicyclic acid, pyridinethione metal salts (e.g., zinc), other 1-hydroxy pyridones such as those described in U.S. Pat. No. 4,185,106, Dellmar et al, issued Jan. 22, 1980, and azole antimycotics disclosed in British Pat. No. 1,502,144, issued Feb. 22, 1918, both patents incorporated herein by reference. When present, this additional anti-dandruff agent comprises from about 0.1% to about 7% of the composition, preferably from about 0.2% to about 2%.

Zinc pyridinethione is preferred, particularly where its salt crystals are predominantly flat platelets which have a mean sphericity less than about 0.65, preferably between about 0.20 and about 0.65 and an individual median particle diameter of at least about 2 microns, expressed as the diameter of a sphere of equivalent volume.

The diameter of a sphere of equivalent volume, $d_v$, for a particle can be determined by a variety of sedimentation techniques which are based on Stokes' law for the setting velocity of a particle in a fluid. Such techniques are described in Stockham U. D. and Fochtman, E. G. *Particle Size Analysis,* Ann Arbor Science, 1978; incorporated herein by reference.

The sphericity of a particle is also described by Stockham and Fochtman, page 113, as $$\psi = \left(\frac{d_v}{d_s}\right)^2$$

where $d_v$ is the diameter of a sphere of equivalent volume, and $d_s$ is the diameter of a sphere of equivalent area. A technique for determining $d_s$ is the BET technique described by Stockham and Fochtman at page 122.

Since the sphericity of interest herein is the mean sphericity, the mean diameters are employed.

Suspension Agent

The lotion shampoo compositions of the invention preferably comprise a suspending agent. The suspending agent useful in the present composition can be one of several agents. Useful are ethylene glycol esters of fatty acids containing from about 16 to about 22 carbon atoms, preferably from about 16 to about 18 carbon atoms.

The ethylene glycol esters found useful in the compositions of the present invention are diesters wherein the esters are a mixture of palmitate and stearate. The amount of stearate should be in the range of about 10% to about 42% or in the range of about 55% to about 80% with palmitate accounting for the remainder. The amount of stearate is preferably from about 60% to about 75%.

Also useful in compositions of the invention are alkanol amides of fatty acids containing from about 16 to about 22 carbon atoms, preferably from about 16 to about 18 carbon atoms. Preferred alkanol amides are stearic monoethanolamide stearic diethanolamide, stearic monoisopropanolamide and stearic monoethanolamide stearate. Another useful group of suspending agents are alkyl dimethylamine oxides, wherein the alkyl group contains from about 16 to about 22 carbon atoms such as stearyldimethyl amine oxide.

Mixtures of the above suspending agents may also be used. Compositions of the invention comprise from about 2% to about 6% of the suspending agent, preferably from about 3% to about 5%.

The shampoo compositions herein can contain a variety of other nonessential optional components suitable for rendering such compositions more acceptable. Such conventional optional ingredients are well known to those skilled in the art, e.g., preservatives such as benzyl alcohol, methyl paraben, propyl paraben, methylisothiazolinone and imidazolidinyl urea; thickeners and viscosity modifiers such as amine oxides, block polymers of ethylene oxide and propylene oxide such as Pluronic F88 offered by BASF Wyandotte, fatty alcohols such as cetearyl alcohol, sodium chloride, ammonium chloride, sodium sulfate, polyvinyl alcohol, propylene glycol and ethyl alcohol; hydrotopes such as xylene sulfonate, amine sulfonate, and polyethylene glycol; pH adjusting agents such as citric acid, succinic acid, phosphoric acid, sodium hydroxide, sodium carbonate, etc.; perfumes; dyes; quaternary ammonium compounds such as Polyquaternium 41; and, sequestering agents such as disodium ethylenediamine tetraacetate. Such agents generally are used individually at a level of from about 0.01% to about 10%, preferably from about 0.01% to about 5.0% by weight of the composition.

The compositions herein are preferably free of clays and polymeric thickeners. By "free" is meant less than about 20 ppm.

METHOD OF MANUFACTURE

Method for manufacturing the present compositions are disclosed in Examples II, III, and IV.

INDUSTRIAL APPLICABILITY

The present shampoo compositions are used in a conventional manner for cleaning hair. From about 0.1 g to about 20 g of a shampoo composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

All percentages are by weight unless otherwise specifically indicated.

EXAMPLES

Example I

The following composition is representative of the present invention.

| Component | Weight % |
| --- | --- |
| Hydrocortisone acetate | 0.50 |
| Triethanolamine alkyl sulfate | 19.40 |
| Water | qs 100% |

Example II

The following composition is representative of the present invention.

| Component | Weight % |
| --- | --- |
| Hydrocortisone acetate | 2.00 |
| Triethanolamine lauryl sulfate | 19.40 |
| Coconut monoethanolamide | 4.00 |
| Ethylene glycol distearate[1] | 5.00 |
| Citric acid | 0.60 |
| Sodium chloride | 0.90 |
| Minors (Perfume, preservative, color) | <1.00 |
| Water | qs 100% |

[1]Ethylene glycol distearate wherein the ester groups are not pure stearate but a mixture of palmitate and stearate in the ratio 35:65 (palmitate:stearate here and hereafter).

The above composition is prepared by mixing part of the water, part of the surfactant, the citric acid, amide, distearate, and dye together in a mix tank and heating the mixture to form about 66° C. to about 88° C. The mixture is then cooled to from about 21° C. to about 49° C. After cooling is completed, the perfume, hydrocortisone acetate, preservative and the remainder of the surfactant and water are added. The total mixture is agitated until a homogeneous mixture is obtained.

Example III

The following is another composition representative of the present invention.

| Component | Weight % |
| --- | --- |
| Hydrocortisone acetate | 1.00 |
| Ammonium lauryl sulfate | 9.00 |
| Ammonium laureth sulfate | 10.00 |
| Ammonium xylene sulfonate | 2.00 |
| Cocoamide MEA | 3.40 |
| Glycol distearate[1] | 3.00 |
| Citric acid | 0.20 |
| Minors (perfume, preservatives, color) | <1.00 |
| Water | qs 100% |

[1]Ethylene glycol distearate wherein the ester groups are not pure stearate but a mixture of palmitate and stearate in the ratio 35:65.

The above composition is prepared by mixing part of the water, part of the surfactant, the citric acid, amide, distearate, and dye together in a mix tank and heating the mixture to from about 66° C. to about 88° C. The mixture is then cooled to from about 21° C. to about 49° C. After cooling is completed, the perfume, hydrocortisone acetate, minor ingredients and the remainder of the surfactant and water are added. The total mixture is agitated until a homogeneous mixture is obtained.

Example IV

The following composition is representative of the present invention.

| Component | Weight % |
| --- | --- |
| Hydrocortisone acetate | 1.00 |
| Glycol distearate[1] | 3.00 |
| Zinc pyridinethione[2] | 1.00 |
| Ammonium lauryl sulfate | 9.00 |
| Ammonium laureth sulfate | 10.00 |
| Ammonium xylene sulfonate | 2.00 |
| Cocoamide MEA | 3.40 |
| Citric acid | 0.20 |
| Minors (perfume, preservatives, color) | <1.00 |
| Water | qs 100% |

[1]Ethylene glycol distearate wherein the ester groups are not pure stearate but a mixture of palmitate and stearate in the ratio 35:65.
[2]ZPT in platelet form having a median particle diameter of about 15 microns The above composition is prepared by mixing part of the water, part of the surfactant, the citric acid, amide, distearate, and dye together in a mix tank and heating the mixture to from about 66° C. to about 88° C. The mixture is then cooled to from about 21° C. to about 49° C. After cooling is completed, the perfume, hydrocortisone acetate, minor ingredients and the remainder of the surfactant and water are added. The total mixture is agitated until a homogeneous mixture is obtained.

Example V

The following composition is another example of the present invention.

| Component | Weight % |
| --- | --- |
| Hydrocortisone acetate | 0.75 |
| Sodium Alkyl Glyceryl Ether Sulfonate | 30.0 |
| Sodium N—Lauroyl Sarcosinate | 4.5 |
| Sodium Chloride | 5.8 |
| Cocoamide DEA | 1.8 |
| N—Cocoyl Sarcosine Acid | 1.0 |
| Minors (perfume, color, preservative) | <1.0 |
| Water | qs 100 |
| | 100.00 |

What is claimed is:

1. A shampoo composition comprising:
   (a) a water-insoluble particulate corticosteroid anti-inflammatory agent consisting of from about 0.2% to about 2% of hydrocortisone acetate;
   (b) from about 5% to about 40% of an anionic surfactant selected from the group consisting of alkyl sulfates, alkyl ether sulfates, and mixtures thereof; and
   (c) water.

2. A lotion shampoo composition according to claim 1 further comprising from about 2% to about 6% of a suspending agent and wherein the organic surfactant is present at a level of from about 15% to about 25%.

3. A lotion shampoo composition according to claim 2 wherein the suspending agent is an ethylene glycol diester wherein the esters are a mixture of palmitate and stearate groups selected from the group consisting of mixtures containing from about 10% to about 42% stearate, mixtures containing from about 55% to about 80% stearate and mixtures thereof.

4. A composition according to claim 1 additionally comprising from about 0.1% to about 2% of an additional anti-dandruff agent selected from the group consisting of pyridinethione metal salts, coal tar, sulfur, selenium sulfide, salicylic acid, 1-hydroxy pyridone, azole antimycotics and mixtures thereof.

5. A composition according to claim 4 wherein the pyridinethione metal salt is zinc pyridinethione.

6. A composition according to claim 1 additionally comprising a 1-hydroxy-2-pyridone in an amount ranging from about 0.1% to about 2%.

7. A lotion shampoo composition according to claim 1 comprising:
   (a) from about 0.1% to about 2% hydrocortisone acetate;
   (b) from about 5% to about 25% of an anionic surfactant selected from the group consisting of alkyl sulfates, alkyl ether sulfates, and mixtures thereof;
   (c) from about 3% to about 5% of an ethylene glycol diester;
   (d) from about 0.1% to about 1% of a pyridinethione metal salt; and
   (e) water.

8. A shampoo composition according to claim 7 wherein the pyridinethione metal salt is zinc pyridinethione.

9. A method of shampooing hair wherein an effective amount of an anti-inflammatory agent is deposited on the scalp comprising the steps of:
   (a) applying from about 0.1 g to about 20 g of a composition according to claim 7 to hair that has been wetted;
   (b) working said composition through said hair; and
   (c) rinsing said composition from said hair.

* * * * *